United States Patent [19]

Lafon

[11] Patent Number: 4,847,274

[45] Date of Patent: Jul. 11, 1989

[54] 4-PHENYLTHIAZOLE DERIVATIVES

[75] Inventor: Louis Lafon, Paris, France

[73] Assignee: Laboratoire L. Lafon, Alfort, France

[21] Appl. No.: 99,485

[22] Filed: Sep. 22, 1987

[30] Foreign Application Priority Data

Oct. 2, 1986 [FR] France .................. 86 13739

[51] Int. Cl.$^4$ ........................................... A61K 31/425
[52] U.S. Cl. .................................... 514/365; 548/193
[58] Field of Search ..................... 548/193; 514/365

[56] References Cited

PUBLICATIONS

Kosary, Pharma, 1987, 42, 373, C.A. 108 94452z.
Chemical Abstracts, vol. 94, No. 23, (Jun. 8, 1981), p. 657, paragraph 94:192274C, (4 pages).

Primary Examiner—Robert Gerstl
Attorney, Agent, or Firm—George H. Gerstman; Garrettson Ellis

[57] ABSTRACT

The present invention relates to 4-phenylthiazole derivatives, namely 2-(2-hydroxyethylamino)-4-phenylthiazole and its addition salts.

These derivatives act on the CNS and are useful as sedatives.

4 Claims, No Drawings

4-PHENYLTHIAZOLE DERIVATIVES

The present invention relates to 4-phenylthiazole derivatives, namely 2-(2-hydroxyethylamino)-4-phenyl-thiazole and its addition salts, the method for their preparation and their use in therapy, in particular as sedatives.

2-(2-Hydroxyethylamino)-4-phenylthiazole is known as a laboratory curiosity from the article by Rastogi et al., Indian J. Chem., Sect. B 19B (11), pages 1003–1005 (1980), as abstracted in CA 94, 192 274c. According to the invention, a therapeutic use of this product and its addition salts is recommended.

The 4-phenylthiazole derivatives according to the invention are therefore selected from the group comprising:

(a) 2-hydroxyethylamino)-4-phenylthiazole of the structural formula:

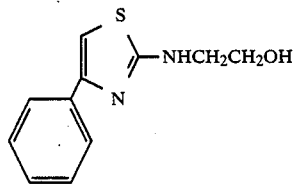

(I)

and (b) its addition salts.

The term "addition salts" is understood here as meaning, on the one hand, the acid addition salts obtained by reacting the free base of the formula I with mineral and organic acids and, on the other hand, the ammonium salts. Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluene-sulfonic acids may be mentioned in particular among the acids which can be used to salify the base of the formula I. ICH$_3$, ClCH$_3$, ICH$_2$C$_6$H$_5$ and ClCH$_2$C$_6$H$_5$ may be mentioned in particular among the compounds with which ammonium salts can be obtained. The acid addition salts are the preferred salts from a therapeutic point of view; among the said acid addition salts, the hydrochloride is one of the most advantageous as a sedative.

A number of typical compounds according to the invention have been collated in Table I below without in any way implying a limitation.

TABLE I

| Product | Code no. | HX |
|---------|----------|-----|
| Ex. 1 | CRL 41108 | HCl |
| Ex. 2 | — | CH$_3$SO$_3$H |
| Ex. 3 | — | ½ fumaric acid |
| Ex. 4 | — | ½ maleic acid |
| Ex. 5 (a) | — | — |

Note
(a) free base 2-(2-Hydroxyethylamino)-4-phenylthiazole and its addition salts can be prepared according to a method known per se by the application of conventional reaction mechanisms. The method which is recommended according to the invention consists in replacing one of the hydrogen atoms of the 2-amino group of 2-amino-4-phenylthiazole with the β-hydroxyethyl group.

The best way of carrying out this method, which is illustrated by scheme A:

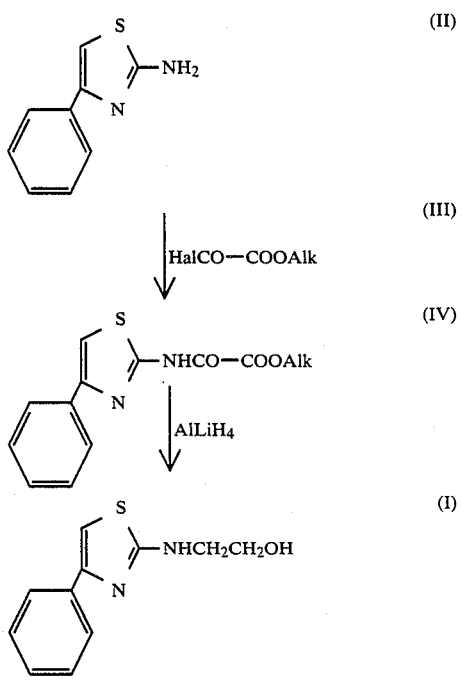

(in which Alk represents a lower alkyl group, especially C$_1$–C$_2$ and preferably the group CH$_2$CH$_3$, and Hal represents a halogen atom, especially F, Cl or Br, the preferred halogen being chlorine), comprises:

(1°) reacting 2-amino-4-phenylthiazole (II) with a halide of a lower alkyl monoester of oxalic acid (III) to give a 2-alkyloxalylamido-4-phenyl-thiazole (IV), and then (2°) reducing the amide and ester groups of the said 2-alkyloxalylamido-4-phenylthiazole (IV), obtained in this way, with AlLiH$_4$.

The reaction II+III→IV of stage (1°) is advantageously carried out in any anhydrous organic solvent, for at least 0.25 h, at a rate of more than one mol of III per mol of II (in particular 1.1 mol of III per mol of II), in the presence of a proton acceptor (especially an organic base such as pyridine or α, β or γ-picoline), it being possible for the said organic base to act as a solvent or co-solvent for the said reaction.

The reaction IV+AlLiH$_4$→I of stage (2°) is carried out in an anhydrous organic solvent (preferably tetrahydrofuran) at a rate of more than two mol of AlLiH$_4$ per mol of IV (in particular 3 mol of AlLiH$_4$ per mol of IV).

The 2-amino-4-phenylthiazole used as the starting material in this method can be prepared by a method which is known or ordinary per se, for example according to the abstract in Chemical Abstracts 60, 4123c or Preparation II below.

It has been found that 2-(2-hydroxyethylamino)-4-phenylthiazole and its addition salts are psychotopic agents; they act on the central nervous system (CNS) as sedatives. According to the invention, a therapeutic composition is recommended which contains, in association with a physiologically acceptable excipient, at least one compound selected from the group comprising 2-(2-hydroxyethylamino)-4-phenyl-thiazole and its non-toxic addition salts.

Of course, in a composition of this kind, the active principle, i.e. in this case 2-(2-hydroxyethyl-amino)-4-phenylthiazole, its non-toxic addition salts and mixtures thereof, is present in a pharmaceutically effective amount.

According to the invention, it is also recommended to use a substance belonging to the group comprising 2-(2-hydroxyethylamino)-4-phenylthiazole and its non-toxic addition salts for the preparation of a sedative drug which is to be used in therapy for the treatment of diseases and pathologies where a sedative is required in order to calm and tranquilize the patients.

Further advantages and characteristics of the invention will be understood more clearly from the following description of preparative examples and results of neuropsychopharmacological tests; these data as a whole do not imply a limitation but are given by way of illustration.

PREPARATION I

Preparation of 2-(2-hydroxyethylamino)-4-phenylthiazole hydrochloride

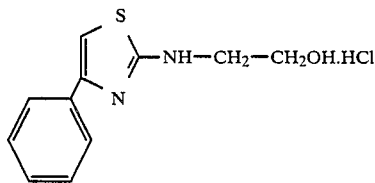

(Example 1; code no.: CRL 41 108)

(a) 2-(Ethyloxalylamido)-4-phenylthiazole 12.3 ml (0.11 mol) of ethyloxalyl chloride (ClCO-COOC$_2$H$_5$; other names: ethyl chloroformylformate, ethyl chlorooxoacetate) are introduced, over a period of 0.5 h, into a solution of 17.6 g (0.10 mol) of 2-amino-4-phenylthiazole in 25 ml of pyridine. The mixture is diluted with 100 ml of acetone and stirred for 0.5 h and the resulting suspension is poured into cold water. The precipitate formed is collected by filtration. Recrystallization from anhydrous ethanol gives 24.8 g (yield: 89.85%) of 2-(ethyloxalylamido)-4-phenylthiazole of the formula;

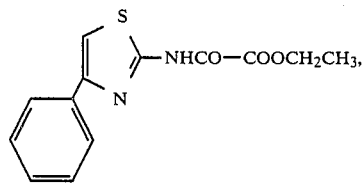

which is in the form of a yellow powder. M.p. (inst.)=159° C. (b) CRL 41 108

A solution of 16.56 g (0.06 mol) of 2-(ethyl-oxalylamido)-4-phenylthiazole [obtained as indicated in stage a) above] in 200 ml of tetrahydrofuran is introduced, over a period of 1.5 h, into a suspension of 6.85 g (0.18 mol) of AlLiH$_4$ in 200 ml of tetrahydrofuran. The resulting mixture is stirred for 1.5 h, the excess AlLiH$_4$ is then neutralized with 36 ml of ethyl acetate and the resulting complexes are decomposed by the successive addition of 6.9 ml of water, 6.9 ml of 4 N sodium hydroxide and 21 ml of water. The insoluble material is removed by filtration, the filtrate is dried over dry sodium sulfate and the said filtrate dried in this way is evaporated to dryness under reduced pressure. The resulting evaporation residue [which contains the 2-(2-hydroxyethylamino)-4-phenyl-thiazole] is treated in diethyl ether with a solution of hydrochloric acid in ethanol and the precipitate formed is purified by 2 successive recrystallizations from isopropanol and acetonitrile, with CXA charcoal treatment, to give 9.5 g (yield: 61.7%; overall yield (a)+(b) : 55.4%) of CRL 41 108 in the form of a water-soluble white powder. M.p.=about 75° C.

PREPARATION II

Preparation of 2-amino-4-phenylthiazole (Code no.: CRL 41 081)

A solution of 19.9 g (0.10 mol) of α-bromo-acetophenone and 11.4 g (0.15 mol) of thiourea in 75 ml of methanol is refluxed for 2 h. It is evaporated to dryness under reduced pressure and the evaporation residue is taken up with water. The resulting solution, heated to the reflux temperature, is treated with CXA charcoal and then rendered alkaline with aqueous ammonia. The precipitate formed is isolated by filtration and purified by recrystallization from isopropanol, with CXA charcoal treatment. to give 15 g (yield: 85.15%) of the expected product in the form of water-insoluble white needles. M.p. (inst.)=150° C.

PREPARATION III

The free base contained in the evaporation residue of stage (b) of Preparation I is isolated. Reaction of the said free base with methanesulfonic acid, fumaric acid and maleic acid gives respectively the methanesulfonate, hemifumarate and hemimaleate of 2-(2-hydroxyethylamino)-4-phenylthiazole (Examples 2-4).

The results of the tests carried out the CRL 41 108 (product of Example 1) according to the invention have been summarized below. In these tests, a solution of CRL 41 108 in distilled water (pH 3.5) was administered intraperitoneally to male mice in a volume of 20 ml/kg and male rats in a volume of 5 ml/kg.

I—TOXICITY

The preliminary toxicity study, which was carried out on groups of 3 animals per dose studied, shows that for intraperitoneal administration to male mice:

the LD$_O$ (maximum non-lethal dose) is greater than 256 mg/kg, the LD$_{100}$ (minimum lethal dose for all the animals) is less than 1024 mg/kg, a dose of 512 mg/kg causes sedation and a decrease in the reactivity to touch and the heart rate and results in the death of 2 out of 3 animals in 0.5 h, and the LD$_{60}$ is of the order of about 500 mg/kg.

II—OVERALL BEHAVIOR AND REACTIVITIES

Groups of three animals are observed before and then 0.25 h, 0.50 h, 1 h, 2 h, 3 h and 24 h after the administration of CRL 41 108. The following observations are made:

(1°) in mice at doses of 2 mg/kg and 8 mg/kg:
no distinct modification of the behavior and reactivities compared with the control group receiving only distilled water;

at a dose of 32 mg/kg:
hypothermia (maximum value: −1.6° C.) apparent for 1 h; and at doses of 64 mg/kg and 128 mg/kg:
sedation,
hypothermia (which has a maximum value of −5° C. for the 128 mg/kg dose and is apparent for 3 h),
a decrease in the breathing rate, and
a decrease in the reactivities, tonicity and muscular strength; and (2°) in rats at doses of 1 mg/kg, 4 mg/kg and 16 mg/kg:
no modification of the behavior and reactivities compared with the control animals, and
variations in the rectal temperature and pupil diameter which are substantially analogous to those of the control animals; and at a dose of 64 mg/kg:
a decrease in the heart rate,
a decrease in the reactivities,
a decrease in the fear reaction,
a decrease in the tonicity and muscular strength, and
hypothermia (maximum value: −1.9° C.) apparent for 1 h.

III—INTERACTION WITH APOMORPHINE (1°) in mice

Groups of 6 mice receive CRL 41 108 by intraperitoneal administration 0.5 h before the subcutaneous injection of 1 mg/kg or 16 mg/kg of apomorphine. It is observed that CRL 41 108 induces hypothermia at doses of 8 mg/kg, 32 mg/kg and 128 mg/kg and aggravates the hypothermia caused by apomorphine, especially at doses of 32 mg/kg and 128 mg/kg, without modifying the righting attitude and the stereotypies.

(2°) in rats:

CRL 41 108 is administered to groups of 6 rats 0.5 h before the subcutaneous injection of 0.5 mg/kg of apomorphine. It is observed that CRL 41 108 does not modify the stereotypies induced by apomorphine.

IV—INTERACTION WITH AMPHETAMINE

Amphetamine (2 mg/kg) is injected intraperitoneally into groups of 6 rats 0.5 h after the administration of CRL 41 108. It is found that, at the highest dose studied (64 mg/kg), CRL 41 108 causes a decrease in the stereotypies induced by amphetamine.

V—INTERACTION WITH RESERPINE

CRL 41 108 is administered to groups of 6 mice 0.5 h before the intraperitoneal injection of 0.5 mg/kg of oxotremorine.

(1°) Action on the temperature

At doses of 8 mg/kg, 32 mg/kg and 128 mg/kg, CRL 41 108 has a hypothermic effect and aggravates the hypothermia induced by oxotremorine after a latency period of 1.5 h.

(2°) Action on the trembling

CRL 41 108 does not modify the trembling due to oxotremorine.

(3°) Action on the peripheral cholinergic symptoms

It is found that CRL 41 108 does not modify the signs of peripheral cholinergic stimulation (salivation, lacrimation, defecation) due to oxotremorine.

VII—ACTION ON THE FOUR PLATE TEST, TRACTION AND ELECTRIC SHOCK

The test is performed on groups of 10 mice 0.5 h after the administration of CRL 41 108.

It is observed that, at dose of 32 mg/kg and 128 mg/kg, CRL 41 108 reduces the number of punished passes, does not cause motor incoordination and does not modify the convulsant and lethal effects of electric shock.

VIII—ACTION ON THE SPONTANEOUS MOTILITY

Half an hour after they have received CRL 41 108, the mice (6 per dose, 12 control animals) are placed in an actimeter, where their motility is recorded for 30 minutes. It is found that, at doses of 32 mg/kg and 128 mg/kg, CRL 41 108 distinctly reduces the spontaneous motor activity of the mice.

IX—ACTION ON THE INTERGROUP AGGRESSIVENESS

After they have stayed for 3 weeks in the two halves of a cage divided by an opaque partition, groups of 3 mice receive CRL 41 108. Half an hour later, the two groups from the same cage are brought together be removal of the partition and the number of fights which occur in 10 minutes is noted.

It is observed that, as from a dose of 0.5 mg/kg, CRL 41 108 causes a statistically significant reduction in the number of fights.

X—ACTION TOWARDS SOME FORMS OF BEHAVIOR PERTURBED BY VARIOUS AGENTS (1°) Motility reduced by habituation of the enclosure After they have stayed for 18 hours in the actimeters, the mice (6 per dose, 12 control animals) receive CRL 41 108. They are immediately returned to their respective enclosures and, half an hour later, their motility is recorded for 30 minutes.

It is noted that CRL 41 108 does not cause a distinct resumption in the motor activity of mice accustomed to their enclosure.

(2°) Motility reduced by hypoxic aggression

Half an hour after they have received CRL 41 108, the mice (10 per dose, 20 control animals) are subjected to acute hypobaric anoxia [pressure reduction of 600 mm Hg (i.e. about $8 \times 10^4$ Pa) in 90 seconds, followed by release of vacuum in 45 seconds] and are then placed in an actimeter, where their motility is recorded for 10 minutes.

It is found that, at the highest dose studied (128 mg/kg), CRL 41 108 causes a slight deterioration in the motor recovery of mice whose activity has been depressed following a brief period in a reduced-pressure enclosure.

(3°) Asphyxiant anoxia

Groups of 10 mice receive CRL 41 108 0.5 h before the intraperitoneal administration of 32 mg/kg of gallamine triiodoethylate (reference curarizing substance).

CRL 41 108 causes practically no modification of the time taken for convulsions and death to occur following asphyxiant anoxia caused by a curarizing agent.

XI—INTERACTION WITH BARBITAL

Half an hour after the administration of CRL 41 108, groups of 10 mice receive an intraperitoneal injection of barbital (220 mg/kg).

It is found that, at the doses used, CRL 41 108 does not modify the duration of the sleep induced by barbital.

XII—ACTION ON THE "BEHAVIORAL DESPAIR"

Half an hour after they have received CRL 41 108, groups of 6 mice are placed in a beaker filled with water to a height of 6 cm. The total period of immobility between the 2nd and 6th minutes following immersion is noted.

It is observed that, at doses of 32 mg/kg and especially 128 mg/kg, CRL 41 108 reduces the period of immobility, due to "despair", of mice which have been forcibly immersed.

XIII—INTERACTION WITH SEROTONIN

The purpose of this test is to investigate the activity of CRL 41 108 in respect of the trembling induced in mice by serotonin (5-hydroxytryptamine or 5-HT) in association with a monoamine oxidase inhibitor (abbreviated to MAOI), which in the present case is nialimide.

Groups of 20 male mice receive nialimide (20 mg/kg) by gastric administration 18 h before the intraperitoneal injection of ($\pm$)-5-HT (20 mg/kg) CRL 41 108 being injected intraperitoneally 30 minutes before the ($\pm$)-5-HT.

Immediately after the injection of ($\pm$)-5-HT, the mice are placed individually in transparent plastic ("Plexiglas") boxes. The generalized trembling, the partial trembling and the head twitches are noted on a yes/no basis for 2.5 h. The total trembling embraces the partial and/or generalized trembling.

It is found that, in mice treated with an MAOI beforehand, CRL 41 108 does not cause generalized trembling to appear after administration of a preliminary dose of ($\pm$)-5-HT. At the highiest dose used (128 mg/kg), CRL 41 108 seems to reduce the total trembling and the head twitches.

The absence of potentiation of the behavioral effects induced by 5-HT in mice makes it improbable that CRL 41 108 undergoes serotoninergic participation in the mechanism responsible for its antiaggressive action in the intergroup aggressiveness test mentioned above.

XIV—CONCLUSIONS

The neuropsychopharmacological study demonstrates that CRL 41 108 is a sedative psychotropic agent which (i) induces a decrease in aggressiveness at a dose which does not reduce the spontaneous motor activity, and (ii) reduces the period of behavioral despair in mice.

In clinical trials, CRL 41 108, as a sedative, has proved to be an excellent calmative for adults. The recommended daily dosage for adults is 2 to 3 gelatin capsules each containing 25 mg of CRL 41 108.

What is claimed is:

1. A therapeutic composition containing, in association with a physiologically acceptable excipient, a sedative effective amount of at least one-4-phenylthiazole compound selected from the group consisting of 2-(2-hydroxyethylamino)-4-phenylthiazole and nontoxic addition salts thereof.

2. A composition as claimed in claim 1, wherein the 4-phenylthiazole compound is 2-(2-hydroxyethylamino)-4-phenylthiazole hydrochloride.

3. A method of a sedative treatment which comprises administering to a human being in need of such a treatment a sedative effective amount of a compound selected from the group consisting of 2-(2-hydroxyethylamino)-4-phenyl-thiazole and non toxic addition salts thereof.

4. The method of claim 3 in which said compound is 2-(2-hydroxyethylamino)-4-phenylthiazole hydrochloride.

* * * * *